US010905087B2

(12) United States Patent
May

(10) Patent No.: US 10,905,087 B2
(45) Date of Patent: Feb. 2, 2021

(54) COTTON VARIETY 16R246NRB2XF

(71) Applicant: MONSANTO TECHNOLOGY LLC, St. Louis, MO (US)

(72) Inventor: O. Lloyd May, Tifton, GA (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 102 days.

(21) Appl. No.: 16/243,515

(22) Filed: Jan. 9, 2019

(65) Prior Publication Data
US 2020/0214241 A1 Jul. 9, 2020

(51) Int. Cl.
*A01H 6/60* (2018.01)
*A01H 5/10* (2018.01)

(52) U.S. Cl.
CPC .............. *A01H 6/604* (2018.05); *A01H 5/10* (2013.01)

(58) Field of Classification Search
CPC .................................................. A01H 6/604
See application file for complete search history.

(56) References Cited

U.S. PATENT DOCUMENTS

| | | | |
|---|---|---|---|
| 4,940,835 A | 7/1990 | Shah et al. | |
| 5,338,544 A | 8/1994 | Donovan | |
| 5,451,514 A | 9/1995 | Boudet et al. | |
| 5,523,520 A | 6/1996 | Hunsperger et al. | |
| 5,633,435 A | 5/1997 | Barry et al. | |
| 5,717,084 A | 2/1998 | Herrera-Estrella et al. | |
| 5,728,925 A | 3/1998 | Herrera-Estrella et al. | |
| 5,850,019 A | 12/1998 | Maiti et al. | |
| 5,981,834 A | 11/1999 | John et al. | |
| 6,051,753 A | 4/2000 | Comai et al. | |
| 6,083,878 A | 7/2000 | Brants et al. | |
| 6,329,570 B1 | 12/2001 | Martineau | |
| 6,489,542 B1 | 12/2002 | Corbin et al. | |
| 6,660,911 B2 | 12/2003 | Fincher et al. | |
| 6,943,282 B1 | 9/2005 | Adang et al. | |
| 6,949,696 B2 | 9/2005 | Fincher et al. | |
| 7,022,896 B1 | 4/2006 | Weeks et al. | |
| 7,064,249 B2 | 6/2006 | Corbin et al. | |
| 7,112,665 B1 | 9/2006 | Leemans et al. | |
| 7,112,725 B2 | 9/2006 | Fincher et al. | |
| 7,141,722 B2 | 11/2006 | Fincher et al. | |
| 7,223,907 B2 | 5/2007 | Huber et al. | |
| 7,381,861 B2 | 6/2008 | Cerny et al. | |
| 7,700,830 B2 | 4/2010 | Corbin et al. | |
| 7,812,224 B2 | 10/2010 | Weeks et al. | |
| 7,855,326 B2 | 12/2010 | Feng et al. | |
| 7,858,764 B1 | 12/2010 | Huber et al. | |
| 7,939,721 B2 | 5/2011 | Arnevik et al. | |
| 8,071,735 B2 | 12/2011 | Cerny et al. | |
| 8,119,380 B2 | 2/2012 | Weeks et al. | |
| 8,207,416 B2 | 6/2012 | Williams | |
| 8,207,418 B2 | 6/2012 | Williams | |
| 8,420,888 B2 | 4/2013 | Feng et al. | |
| 8,435,743 B2 | 5/2013 | Cerny et al. | |
| 8,629,323 B2 | 1/2014 | Weeks et al. | |
| 8,735,661 B2 | 5/2014 | Brinker et al. | |
| 9,024,115 B2 | 5/2015 | Brinker et al. | |
| 9,133,473 B2 | 9/2015 | Huber et al. | |
| 9,307,734 B2* | 4/2016 | Bhatti | A01H 5/10 |
| 9,585,348 B2 | 3/2017 | May | |
| 9,963,714 B1 | 5/2018 | May | |
| 2018/0251777 A1 | 9/2018 | May | |

FOREIGN PATENT DOCUMENTS

WO WO 2004/072235 8/2004

OTHER PUBLICATIONS

Bowman et al., "Pedigrees of Upland and Pima Cotton Cultivars Released Between 1970 2005," Mississippi Agricultural & Forestry Experiment Station, Bulletin 1155, Dec. 2006.
Eshed et al., "Less-than-addictive epistatic interactions of quantitative trait loci in tomato," *Genetics*, 143:1807-1817, 1996.
Fehr (ed), "Backcross Method," In: Principles of Cultivar Development, vol. 1: Theory and Technique, pp. 360-376, 1987.
Kraft et al., "Linkage disequilibrium and fingerprinting in sugar beet," *Theor. Appl. Genet.*, 101:323-326, 2000.
Poehlman (ed), "Breeding Corn (Maize)," In: Breeding Field Crops, 3rd Ed., AVI Publishing Company, Westport, Connecticut, pp. 469-481, 1987.
Poehlman (eds), "Backcross Breeding," In: Breeding Field Crops, 4th Ed., pp. 172-175, 1995.
Rieger et al., In: Glossary of Genetics and Cytogenetics, Classical and Molecular, Springer-Verlag, Berlin, p. 116, 1976.
Sprague et al. (Eds.), "8-1.1.2 Backcrossing," In: Corn and Improvement, 3rd Ed., Madison, WI, pp. 472-473, 1998.
Marchosky et al., "Bollgard® and Bollgard II® Efficacy in Near Isogenic Lines of 'DP50' Upland Cotton in Arizona," Arizona Cotton Report, The University of Arizona College of Agriculture and Life Sciences, 2001.
Phipps et al., "Performance of Roundup Flex © cotton varieties in the North Mississippi River Delta," pp. 874-880, 2006 Beltwide Cotton Conferences, San Antonio, Texas, Jan. 3-6, 2006.
Virginia Cotton Production Guide 2011, College of Agriculture and Life Sciences, Virginia Tech, 2011.
Variety specific information as indicated in transmittal letter of Feb. 28, 2019 Information Disclosure Statement for U.S. Appl. No. 16/243,515.

* cited by examiner

*Primary Examiner* — David H Kruse
(74) *Attorney, Agent, or Firm* — Dentons US LLP

(57) ABSTRACT

The invention relates to the novel cotton variety designated 16R246NRB2XF. Provided by the invention are the seeds, plants, plant parts and derivatives of the cotton variety 16R246NRB2XF. Also provided by the invention are methods of using cotton variety 16R246NRB2XF and products derived therefrom. Still further provided by the invention are methods for producing cotton plants by crossing the cotton variety 16R246NRB2XF with itself or another cotton variety and plants and seeds produced by such methods.

20 Claims, No Drawings

US 10,905,087 B2

COTTON VARIETY 16R246NRB2XF

BACKGROUND OF THE INVENTION

Field of the Invention

The present invention relates generally to the field of cotton breeding. In particular, the invention relates to the novel cotton variety 16R246NRB2XF.

Description of Related Art

The goal of a commercial cotton breeding program is to develop new, unique and superior cotton varieties. In cotton, important traits include, but are not limited to, higher fiber (lint) yield, earlier maturity, improved fiber quality, resistance to diseases and insects, tolerance to drought and heat, and improved agronomic traits. The breeder selects and crosses two or more lines, followed by generation advancement and selection, thus producing many new genetic combinations. The breeder can theoretically generate billions of different genetic combinations via this procedure.

SUMMARY OF THE INVENTION

One aspect of the present invention relates to seed of the cotton variety 16R246NRB2XF. The invention also relates to plants produced by growing the seed of the cotton variety 16R246NRB2XF as well as the derivatives of such plants. As used herein, the term "plant" includes plant cells, plant protoplasts, plant cells of a tissue culture from which cotton plants can be regenerated, plant calli, plant clumps, and plant cells that are intact in plants or parts of plants, such as pollen, flowers, seeds, bolls, leaves, stems, and the like.

Another aspect of the invention relates to a tissue culture of regenerable cells of the cotton variety 16R246NRB2XF as well as plants regenerated therefrom, wherein the regenerated cotton plant is capable of expressing all of the morphological and physiological characteristics of a plant grown from the cotton seed designated 16R246NRB2XF.

Yet another aspect of the current invention is a cotton plant of the cotton variety 16R246NRB2XF further comprising a single locus conversion. In one embodiment, the cotton plant is defined as comprising the single locus conversion and otherwise capable of expressing all of the morphological and physiological characteristics of the cotton variety 16R246NRB2XF. In particular embodiments of the invention, the single locus conversion may comprise a transgenic gene which has been introduced by genetic transformation into the cotton variety 16R246NRB2XF or a progenitor thereof. A transgenic or non-transgenic single locus conversion can also be introduced by backcrossing, as is well known in the art. In certain embodiments of the invention, the single locus conversion may comprise a dominant or recessive allele. The locus conversion may confer potentially any trait upon the plant as described herein. In specific embodiments of the invention, a locus conversion may confer one or more traits such as, for example, male sterility, herbicide tolerance, insect resistance, disease resistance, waxy starch, modified fatty acid metabolism, modified phytic acid metabolism, modified carbohydrate metabolism and modified protein metabolism. In certain embodiments, a potential locus conversion that confers herbicide resistance may confer resistance to herbicides such as, for example, imidazolinone herbicides, sulfonylurea herbicides, triazine herbicides, phenoxy herbicides, cyclohexanedione herbicides, benzonitrile herbicides, 4-hydroxyphenylpyruvate dioxygenase-inhibiting herbicides, protoporphyrinogen oxidase-inhibiting herbicides, acetolactate synthase-inhibiting herbicides, 1-aminocyclopropane-1-carboxylic acid synthase-inhibiting herbicides, bromoxynil, nicosulfuron, 2,4-dichlorophenoxyacetic acid (2,4-D), dicamba, quizalofop-p-ethyl, glyphosate, or glufosinate.

In another aspect of the invention, a plant of cotton variety 16R246NRB2XF is provided further comprising a transgene. The transgene may comprise a naturally occurring cotton gene or recombinant DNA. In certain embodiments of the invention, the transgene confers traits such as, for example, male sterility, waxy starch, herbicide resistance, insect resistance, resistance to bacterial, fungal, nematode or viral disease, and altered fatty acid, phytate, or carbohydrate metabolism.

Still yet another aspect of the invention relates to a method of generating a plant of cotton variety 16R246NRB2XF with a modified genome by introducing a transgene or single locus conversion. A transgenic or non-transgenic single locus conversion can be introduced by backcrossing, as is well known in the art. The transgene may be introduced through genetic transformation techniques, as are also well known in the art.

Still yet another aspect of the invention relates to a first generation ($F_1$) hybrid cotton seed produced by crossing a plant of the cotton variety 16R246NRB2XF to a second cotton plant. Also included in the invention are the $F_1$ hybrid cotton plants grown from the hybrid seed produced by crossing the cotton variety 16R246NRB2XF to a second cotton plant. Still further included in the invention are the seeds produced by $F_1$ hybrid plants, which have a plant of the cotton variety 16R246NRB2XF as one parent; the second generation ($F_2$) hybrid cotton plants grown from the seeds produced by those $F_1$ hybrid plants; and the seeds produced by those $F_2$ hybrid plants.

In a further aspect of the invention, a composition is provided comprising a seed of cotton variety 16R246NRB2XF comprised in plant seed growth media. In certain embodiments, the plant seed growth media is a soil or synthetic cultivation media. In specific embodiments, the growth media may be comprised in a container or may, for example, be soil in a field. Plant seed growth media are well known to those of skill in the art and include, but are in no way limited to, soil or synthetic cultivation media. Plant seed growth media can provide physical support for seeds and can retain moisture and/or nutritional components. Examples of characteristics for soils in certain embodiments can be found, for instance, in U.S. Pat. Nos. 3,932,166 and 4,707,176. Synthetic plant cultivation media are also well known in the art and may, in certain embodiments, comprise polymers or hydrogels. Examples of such compositions are described, for example, in U.S. Pat. No. 4,241,537.

Still yet another aspect of the invention is a method of producing cotton seeds comprising crossing a plant of the cotton variety 16R246NRB2XF to any second cotton plant, including itself or another plant of the variety 16R246NRB2XF. In particular embodiments of the invention, the method of crossing comprises: (a) planting seeds of the cotton variety 16R246NRB2XF; (b) cultivating cotton plants resulting from said seeds until said plants bear flowers; (c) allowing fertilization of the flowers of said plants; and (d) harvesting seeds produced from said plants.

Still yet another aspect of the invention is a method of producing hybrid cotton seeds comprising crossing the cotton variety 16R246NRB2XF to a second, distinct cotton plant which can be nonisogenic to the cotton variety 16R246NRB2XF. In particular embodiments of the invention, the crossing comprises: (a) planting seeds of cotton variety 16R246NRB2XF and a second, distinct cotton plant; (b) cultivating the cotton plants grown from the seeds until the plants bear flowers; (c) cross-pollinating a flower on one of the two plants with the pollen of the other plant; and (d) harvesting the seeds resulting from the cross-pollinating.

Still yet another aspect of the invention is a method for developing a cotton plant in a cotton breeding program comprising: (a) obtaining a cotton plant, or its parts, of the variety 16R246NRB2XF; and (b) employing said plant or parts as a source of breeding material using plant breeding techniques. In the method, the plant breeding techniques include, but are not limited to, recurrent selection, mass selection, bulk selection, backcrossing, pedigree breeding, genetic marker-assisted selection and genetic transformation. In certain embodiments of the invention, the cotton plant of variety 16R246NRB2XF is used as the male or female parent.

Still yet another aspect of the invention is a method of producing a cotton plant derived from the cotton variety 16R246NRB2XF, the method comprising the steps of: (a) preparing a progeny plant derived from cotton variety 16R246NRB2XF by crossing a plant of the cotton variety 16R246NRB2XF with a second cotton plant; and (b) crossing the progeny plant with itself or a second plant to produce a progeny plant of a subsequent generation which is derived from a plant of the cotton variety 16R246NRB2XF. In one embodiment of the invention, the method further comprises: (c) crossing the progeny plant of a subsequent generation with itself or a second plant; and (d) repeating steps (b) and (c) for at least 2-10 additional generations to produce an inbred cotton plant derived from the cotton variety 16R246NRB2XF. Also provided by the invention is a plant produced by this and the other methods of the invention. Plant variety 16R246NRB2XF-derived plants produced by this and the other methods of the invention described herein may, in certain embodiments of the invention, be further defined as comprising the traits of plant variety 16R246NRB2XF given in Table 1.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides, in one aspect, methods and composition relating to plants, seeds and derivatives of the cotton variety 16R246NRB2XF. Cotton variety 16R246NRB2XF was developed from an initial cross of 14Y1420B2R2*2//(10Y0402*4/08Y549B2R2)/ (08Y619B2R2*2/DP0912-BRD-BC 1-F2-0132). The breeding history of the variety can be summarized as follows:

| Generation | Year | Description |
| --- | --- | --- |
| Cross | 2009 | Cross was made in Costa Rica between donor parent 08Y549B2R2 (containing the gene events MON 15985 and MON 88913) and conventional recurrent parent 10Y0402. |
| Backcross | 2009 | Cross was made in Costa Rica using an F1 plant and 10Y0402 plants genotyped to be homozygous for RKN1 (naturally occurring gene that confers resistance to root-knot nematode caused by *Meloidogyne incognita*) as the RP. |
| Backcross | 2010 | BC1F1 plants were genotyped for RKN1 and used in a backcross with the RP to create the BC2F1 in Costa Rica. |
| Backcross | 2010 | BC2F1 plants were genotyped for RKN1 and for MAS recovery of the recurrent parent and used in a backcross with the RP to create the BC3F1 in Costa Rica. |
| BC3F1 | 2011 | BC3F1 plants were genotyped for RKN1 and for MAS recovery of the recurrent parent, and self pollinated in Costa Rica. |
| BC3F2 | 2011 | BC3F2 plants of the 10Y0402*4/08Y549B2RF pedigree were selected for selfing and bulk harvest based on gene purity (MON 15985, MON 88913, RKN1), homozygosity, and MAS recovery of the recurrent parent. |
| BC3F3 | 2012 | BC3F3 progeny rows were planted in the field in Leland, MS for phenotypic evaluation. |
| Composite Cross | 2012 | Selected BC3F3 progeny rows were advanced for crossing in Juana Diaz, PR with BC2F2 plants from the pedigree [08Y619B2R2*2/ DP0912-BRD-BC1-F2-0132] (developed in a similar manner as described herein) containing the gene event MON 88701 for dicamba and glufosinate tolerance. |
| Composite Cross | 2013 | The composite cross F1 plants from 10Y0402*4/08Y549B2R2)/(08 Y619B2R2*2/DP0912-BRD-BC1-F2-0132 were genotyped for RKN1, MON 15985, MON 88913, and MON 8870 and selected plants were crossed with 14Y1420B2R2 as the RP. |
| Composite cross BC1F1 | 2013 | Composite cross BC1F1 plants were genotyped for RKN1, MON 15985, MON 88913, MON 8870, and MAS recovery of the 14Y1420B2R2 RP. Selected plants were self pollinated in Juana Diaz, PR. |
| BC1F2 | 2014 | BC1F2 plants were planted as progeny rows in Leland, MS for agronomic selection. |

-continued

| Generation | Year | Description |
|---|---|---|
| BC1F3 | 2014 | Selected progeny rows were bulk harvested and sent to Costa Rica for winter increase. |
| BC1F4 | 2015 | Replicated field trials were conducted at 40 locations across the cotton belt in the presence of root-knot nematodes and in broad-acre field trials. |
| BC1F5 | 2016 | Replicated field trials were conducted at 32 locations across the cotton belt in the presence of root-knot nematodes and in large block, on-farm broad-acre field trials. One line was designated 16R246NRB2XF. |

| Generation | Year | Selection |
|---|---|---|
| BC1F6 | 2017 | Grown in replicated trials and selected based on the lint yield, lint percent, fiber quality. |
| BC1F7 | 2018 | Grown in replicated trials and selected based on the lint yield, lint percent, fiber quality. |

The cotton variety 16R246NRB2XF has been judged to be uniform for breeding purposes and testing; can be reproduced by planting and growing seeds of the variety under self-pollinating or sib-pollinating conditions, as is known to those of skill in the agricultural arts; and shows no variants other than what would normally be expected due to environment or that would occur for almost any characteristic during the course of repeated sexual reproduction. The results of an objective description of the variety are presented below in Table 1. Those of skill in the art will recognize that these are typical values that may vary due to environment and that other values that are substantially equivalent are within the scope of the invention.

TABLE 1

Phenotypic Description of Variety 16R246NRB2XF

| CHARACTERISTIC | VALUE |
|---|---|
| AREAS OF ADAPTATION | |
| 1. | Eastern |
| 2. | Delta |
| 3. | Central |
| 4. | Plains |
| 5. | Western |
| GENERAL PLANT TYPE | |
| Plant Habit | Intermediate |
| Foliage | Intermediate |
| Stem Lodging | Erect |
| Fruiting Branch | Normal |
| Growth | Intermediate |
| Leaf Color | Medium green |
| Boll Shape | Length more than width |
| Boll Breadth | Broadest at middle |
| MATURITY | |
| Days till maturity | 123 |
| PLANT | |
| cm to 1$^{st}$ Fruiting Branch (from cotyledonary node) | 21.7 |
| No. of Nodes to 1st Fruiting Branch (excluding cotyledonary node) | 5.1 |
| Mature Plant Height in cm (from cotyledonary node to terminal) | 102.2 |

TABLE 1-continued

Phenotypic Description of Variety 16R246NRB2XF

| CHARACTERISTIC | VALUE |
|---|---|
| LEAF (Upper most, fully expanded leaf) | |
| Type | Normal |
| Pubescence | Medium |
| Nectaries | Present |
| STEM | |
| Stem Pubescence | Intermediate |
| GLANDS (Gossypol) | |
| Leaf | Normal |
| Stem | Normal |
| Calyx Lobe (normal is absent): | Normal |
| FLOWER | |
| Petals | Cream |
| Pollen | Cream |
| Petal Spot | Absent |
| SEED | |
| Seed Index (g/100 seeds, fuzzy basis) | 9.8 |
| BOLL | |
| Lint percent (%), Picked | 40.7 |
| Number of seeds per boll | 29.9 |
| Boll Type | Open |
| FIBER PROPERTIES | |
| Specify Method (HVI or other) | HVI |
| Length (inches, 2.5% SL) | 1.17 |
| Uniformity (%) | 83.0 |
| Strength, T1 (g/tex) | 30.7 |
| Elongation, E1 (%) | 8.6 |
| Micronaire | 4.77 |

These are typical values. Values may vary due to environment. Other values that are substantially equivalent are within the scope of the invention.

Cotton variety 16R246NRB2XF is a Bollgard II® Xtend-Flex® insect-protected and herbicide-tolerant cotton variety, as a result of containing events MON 88701, MON 88913, and MON 15985. Event MON 88701 confers dicamba and glufosinate tolerance by producing a dicamba monooxygenase from *Stenotrophomonas maltophilia* and a phosphinothricin acetyltransferase from *Streptomyces hygroscopicus* and is the subject of U.S. Pat. No. 8,735,661, the disclosure of which is incorporated herein by reference.

Event MON 88701 is also covered by one or more of the following patents: U.S. Pat. Nos. 9,024,115; 8,735,661; 8,629,323; 8,420,888; 8,119,380; 7,939,721; 7,855,326; 7,812,224; 7,112,665; 7,022,896; 5,850,019; 5,728,925; and 5,717,084 Event MON 88913 confers glyphosate tolerance by producing a 5-enolpyruvylshikimate-3-phosphate synthase protein from *Agrobacterium* sp. strain CP4 and is the subject of U.S. Pat. No. 7,381,861, the disclosure of which is incorporated herein by reference. Event MON 88913 is also covered by one or more of the following patents: U.S. Pat. Nos. 8,435,743; 8,071,735; 7,141,722; 7,112,725; 6,949,696; 6,660,911; 6,083,878; 6,051,753; 5,728,925; and 5,717,084. Event MON 15985 protects plants from feeding damage caused by lepidopteran insects by producing *Bacillus thuringiensis* Cry1Ac and Cry2Ab proteins and is the subject of U.S. Pat. No. 7,223,907, the disclosure of which is incorporated herein by reference. Event MON 15985 is also covered by one or more of the following patents: U.S. Pat. Nos. 9,133,473; 7,858,764; 7,700,830; 7,064,249; 6,943,282; 6,489,542; 5,728,925; and 5,717,084.

The performance characteristics of cotton variety 16R246NRB2XF were also analyzed and comparisons were made with other distinct varieties. The results of the analysis are presented below in Table 2.

stage in a backcrossing protocol during the production of a single locus conversion of the cotton variety 16R246NRB2XF.

The variety of the present invention is suited to the development of new varieties based on the nature of the genetic background of the variety. In selecting a second plant to cross with 16R246NRB2XF for the purpose of developing novel cotton varieties, it will typically be desired to choose plants that exhibit one or more selectable characteristics. Examples of selectable characteristics include, but are not limited to, higher fiber (lint) yield, earlier maturity, improved fiber quality, resistance to diseases and insects, tolerance to drought and heat, and improved agronomic traits.

Any time the cotton variety 16R246NRB2XF is crossed with another, different, variety, first generation ($F_1$) cotton progeny are produced. The hybrid progeny are produced regardless of characteristics of the two parental varieties used to produce the hybrid progeny. As such, an $F_1$ hybrid cotton plant may be produced by crossing 16R246NRB2XF with any second cotton plant. The second cotton plant may be genetically homogeneous, for example, inbred, or heterogeneous, for example, a hybrid. Any $F_1$ hybrid cotton

TABLE 2

Performance Data for Variety 16R246NRB2XF

| Entries Compared | YLD_BE | LP | MIC | LNTH | UNIF | STRN | EL | LFHAR | FMATR | BOP |
|---|---|---|---|---|---|---|---|---|---|---|
| 16R246NRB2XF | 1,411 | 41.06 | 4.77 | 1.17 | 82.97 | 30.68 | 8.61 | 4.5 | 85.75 | 55 |
| DP 1454NR B2RF | 1,439 | 42.74 | 4.56 | 1.14 | 82.1 | 30.43 | 8.08 | 4.3 | 85.71 | 49 |
| Deviation | −28.03 | −1.68 | 0.21 | 0.03 | 0.87 | 0.25 | 0.53 | 0.25 | 0.04 | 6.26 |
| Significance | * | ** | ** | ** | ** |  | ** |  |  | ** |
| # Obs | 162 | 166 | 117 | 116 | 118 | 118 | 97 | 9 | 97 | 65 |
| Years | 3 | 3 | 3 | 3 | 3 | 3 | 3 | 3 | 3 | 3 |
| Win Percent | 41 | 7 | 18 | 87 | 80 | 64 | 80 | 33 | 57 | 15 |
| Test Mean | 1,347 | 40.94 | 4.43 | 1.17 | 82.71 | 30.32 | 8.14 | 3.9 | 85.31 | 61 |
| 16R246NRB2XF | 1,388 | 40.82 | 4.7 | 1.17 | 82.81 | 29.97 | 8.71 | 4.3 | 85.48 | 55 |
| DP 1823NR B2XF | 1,324 | 41.04 | 4.05 | 1.17 | 82.83 | 29.84 | 9.19 | 4.9 | 83.56 | 67 |
| Deviation | 63.73 | −0.23 | 0.65 | −0 | −0.02 | 0.13 | −0.47 | −0.56 | 1.92 | −12.07 |
| Significance | ** | + | ** |  |  |  | ** | * | ** | ** |
| # Obs | 115 | 119 | 77 | 76 | 78 | 78 | 72 | 8 | 72 | 55 |
| Years | 3 | 3 | 3 | 3 | 3 | 3 | 3 | 3 | 3 | 3 |
| Win Percent | 63 | 34 | 5 | 49 | 45 | 56 | 21 | 83 | 99 | 91 |
| Test Mean | 1,321 | 40.77 | 4.34 | 1.17 | 82.55 | 29.79 | 8.24 | 3.7 | 84.9 | 62 |

**, *, + Significant at P < 0.01, 0.05, or 0.10, respectively

Observations:
YLD_BE—Yield Best Estimate
LP—Percent Lint
MIC—Micronaire
LNTH—Fiber Length
UNIF—Uniformity Index
STRN—Fiber Strength
EL—Elongation
LFHAR—Leaf Hairs-Trichomes
FMATR—Fiber Maturity Ratio
BOP—Bolls Open Percent Breeding Cotton Variety 16R246NRB2XF One aspect of the current invention concerns methods for crossing the cotton variety 16R246NRB2XF with itself or a second plant and the seeds and plants produced by such methods. These methods can be used for propagation of the cotton variety 16R246NRB2XF, or can be used to produce hybrid cotton seeds and the plants grown therefrom. A hybrid plant can be used as a recurrent parent at any given plant produced by crossing cotton variety 16R246NRB2XF with a second cotton plant is therefore a part of the present invention.

Cotton plants can be crossed, for example, by either natural or mechanical techniques. Natural pollination occurs in cotton either by self-pollination or natural cross-pollination, which typically is aided by pollinating organisms. In either natural or artificial crosses, flowering and flowering time are important considerations.

The cotton flower is perfect in that the male and female structures are in the same flower. The crossed or hybrid seed can be produced by manual crosses between selected parents. Floral buds of the parent that is to be the female can be emasculated prior to the opening of the flower by manual removal of the male anthers. At flowering, the pollen from flowers of the parent plants designated as male, can be manually placed on the stigma of the previous emasculated flower. Seed developed from the cross is known as first generation ($F_1$) hybrid seed. Planting of this seed produces $F_1$ hybrid plants of which half their genetic component is from the female parent and half from the male parent.

Segregation of genes begins at meiosis thus producing second generation ($F_2$) seed. Assuming multiple genetic differences between the original parents, each $F_2$ seed has a unique combination of genes.

Self-pollination occurs naturally in cotton with no manipulation of the flowers. For the crossing of two cotton plants, it may be beneficial to use artificial hybridization. In artificial hybridization, the flower used as a female in a cross is manually cross-pollinated prior to maturation of pollen from the flower, thereby preventing self-fertilization, or alternatively, the male parts of the flower can be emasculated using a technique known in the art. Techniques for emasculating the male parts of a cotton flower include, for example, physical removal of the male parts, use of a genetic factor conferring male sterility, and application of a chemical gametocide to the male parts.

For artificial hybridization employing emasculation, flowers that are expected to open the following day are selected on the female parent. The buds are swollen and the corolla is just visible through the calyx or has begun to emerge. Usually no more than two buds on a parent plant are prepared, and all self-pollinated flowers or immature buds are removed with forceps. Special care is required to remove immature buds that are hidden under the stipules at the leaf axil, and could develop into flowers at a later date. The flower is grasped between the thumb and index finger and the location of the stigma determined by examining the sepals. The calyx is removed by grasping a sepal with the forceps, pulling it down and around the flower, and repeating the procedure until the five sepals are removed. The exposed corolla is removed with care to avoid injuring the stigma. Cross-pollination can then be carried out using, for example, petri dishes or envelopes in which male flowers have been collected. Desiccators containing calcium chloride crystals can be used in some environments to dry male flowers to obtain adequate pollen shed.

Either with or without emasculation of the female flower, hand pollination can be carried out by removing the stamens and pistil from a flower of the male parent with a forceps and gently brushing the anthers against the stigma of the female flower. Access to the stamens can be achieved by removing the front sepal and keel petals, or piercing the keel with closed forceps and allowing them to open and push the petals away. Brushing the anthers on the stigma causes them to rupture, and the highest percentage of successful crosses is obtained when pollen is clearly visible on the stigma. Pollen shed can be checked by tapping the anthers before brushing the stigma. Several male flowers may have to be used to obtain suitable pollen shed when conditions are unfavorable, or the same male may be used to pollinate several flowers with good pollen shed.

Cross-pollination is more common within rows than between adjacent rows; therefore, it may be beneficial to grow populations with genetic male sterility on a square grid to create rows in all directions. For example, single-plant hills on 50-cm centers may be used, with subdivision of the area into blocks of an equal number of hills for harvest from bulks of an equal amount of seed from male-sterile plants in each block to enhance random pollination.

There are numerous steps in the development of any novel plant germplasm. Plant breeding usually begins with the analysis and identification of the problems and weaknesses of the current germplasm, the establishment of program goals, and the definition of breeding objectives. The next step is selection of germplasm that possess the traits that meet the program goals. The goal is typically to combine in a single variety a combination of selected traits from the parental germplasm. These traits may include, but are not limited to, resistance to diseases and insects, tolerance to drought and heat, tolerance to herbicides, improvements in fiber traits, and agronomic traits.

Choice of breeding or selection methods depends on the mode of plant reproduction, the heritability of the selected trait(s), and the type of variety used commercially (e.g., $F_1$ hybrid variety, pureline variety, etc.). For heritable traits, especially highly heritable traits, a choice of individual plants evaluated at a single location will be effective; whereas, for traits with low heritability, selection should be based on mean values obtained from replicated evaluations of families of related plants. Popular selection methods commonly include, but are not limited to, pedigree selection, modified pedigree selection, mass selection, recurrent selection and backcrossing.

The complexity of inheritance typically influences the choice of the breeding method. Backcross breeding is used to transfer one or more genetic loci for a heritable trait into a variety. This approach can be used, for example, to breed disease-resistant plant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of offspring from each cross.

Each breeding program may include an objective evaluation of the efficiency of the breeding procedure. Evaluation criteria vary depending on the goal and objectives, but can include gain from selection per year based on comparisons to an appropriate standard, overall value of the advanced breeding lines, and number of successful varieties produced per unit of input (e.g., per year, per dollar expended, etc.).

Promising advanced breeding lines are thoroughly tested and compared to appropriate standards in environments representative of the commercial target area(s) for generally three or more years. The best lines are candidates for new commercial varieties, and those deficient in one or more traits may be used as parents to produce new populations for further selection.

These processes, which lead to the final step of marketing and distribution, may take as much as eight to 12 years from the time the first cross is made. Therefore, development of new varieties is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying these plants is to observe their performance relative to other experimental plants and to one or more widely grown standard varieties. Single observations are generally inconclusive, while replicated observations provide a better estimate of genetic worth.

The goal of plant breeding is to develop new, unique and superior cotton varieties. The breeder selects and crosses two or more parental lines, followed by repeated selfing and selection that produces many new genetic combinations. Each year, the plant breeder selects the germplasm to advance to the next generation. This germplasm is grown under unique and different geographical, climatic and soil conditions, and further selections are then made, during and at the end of the growing season. It is unpredictable which varieties will be eventually developed at the end of these processes. This unpredictability is because the breeder's selection occurs in unique environments, with no control at the DNA level (using conventional breeding procedures), and yields millions of different possible genetic combinations. A breeder of ordinary skill in the art cannot predict the final resulting lines he develops, except possibly in a very gross and general fashion. The same breeder cannot produce the same variety twice by using the exact same original parents and the same selection techniques. This unpredictability results in the expenditure of large amounts of research monies to develop novel cotton varieties.

Pureline cultivars, such as generally used in cotton and many other crops, are commonly bred by hybridization of two or more parents followed by selection. The complexity of inheritance, the breeding objectives and the available resources influence the breeding method. The development of new varieties requires development and selection, the crossing of varieties and selection of progeny from superior crosses.

Pedigree breeding and recurrent selection breeding methods are used to develop varieties from breeding populations. Breeding programs combine traits from two or more varieties or various broad-based sources into breeding pools from which varieties are developed by selfing and selection of phenotypes. The new varieties are evaluated to determine which have commercial potential.

Pedigree breeding can be used with self-pollinating crops. Two parents which possess favorable, complementary traits are crossed to produce an $F_1$. An $F_2$ population is produced by selfing one or several $F_1$ plants. Selection of individuals may begin in the $F_2$ population or later depending upon objectives of the breeder; then, beginning in the $F_3$, individuals from families can be selected. Replicated testing of families can begin in the $F_3$ or $F_4$ generation to improve the effectiveness of selection for traits, especially those with low heritability. At an advanced stage of inbreeding (i.e., $F_6$ and $F_7$), the lines or mixtures of phenotypically similar lines are typically tested for potential release as new varieties.

Mass and recurrent selections can be used with either self- or cross-pollinating crops. A genetically variable population of heterozygous individuals is either identified or created by intercrossing several different parents. Plants are selected based on individual traits, outstanding progeny, or combining ability. The selected plants are intercrossed to produce a new population for which further cycles of selection are continued.

The single-seed descent procedure in the strict sense refers to planting a segregating population, harvesting a sample of one seed per plant, and using the one-seed samples to plant the next generation. When the population has been advanced from the $F_2$ to the desired level of inbreeding, the plants from which the lines are derived will each trace to different $F_2$ individuals. The number of plants in a population declines each generation due to failure of some seeds to germinate or some plants to produce at least one seed. As a result, not all of the $F_2$ plants originally sampled in the population will be represented when generation advance is completed.

The modified single-seed descent procedures involve harvesting multiple seed, for example, using a single lock or a simple boll, from each plant in a population and combining them to form a bulk. Part of the bulk is used to plant the next generation and part is put in reserve. This procedure has been used to save labor at harvest and to maintain adequate seed quantities of the population. The multiple-seed procedure may be used to save labor. It is faster to gin bolls with a machine than to remove one seed by hand. Using the multiple-seed procedure also makes it possible to plant the same number of seeds of a population each generation of inbreeding, as enough seeds are harvested to make up for the plants that did not germinate or produce seed.

Descriptions of other breeding methods that are commonly used for different traits and crops can be found in one of several reference books (e.g., Allard, In: *Principles of plant breeding*, John Wiley & Sons, NY, University of California, Davis, Calif., 50-98, 1960; Simmonds, In: *Principles of crop improvement*, Longman, Inc., NY, 369-399, 1979; Sneep and Hendriksen, In: *Plant breeding perspectives*, Wageningen (Ed), Center for Agricultural Publishing and Documentation, 1979; Fehr, In: *Principles of variety development*, Theory and Technique (Vol 1) and Crop Species Soybean (Vol 2), Iowa State Univ., Macmillian Pub. Co., NY, 360-376, 1987; Fehr, In: *Soybeans: Improvement, Production and Uses,* 2d Ed., *Manograph* 16:249, 1987). Additionally, with any of the methods disclosed above, mutagenesis can be utilized to increase the diversity of the gene pool that is available in the breeding program.

Proper testing should detect faults and establish the level of superiority or improvement over current varieties. In addition to showing superior performance, there must be a demand for a new variety that is compatible with industry standards or which creates a new market. The introduction of a new variety will incur additional costs to the seed producer, the grower, processor and consumer; for special advertising and marketing, altered seed and commercial production practices, and new product utilization. The testing preceding release of a new variety should take into consideration the research and development costs as well as the technical superiority of the final variety. For seed-propagated varieties, it must be feasible to produce seed easily and economically.

In addition to phenotypic observations, a plant can also be characterized by its genotype. The genotype of a plant can be determined by molecular marker profiling, which can be applied to plants of the same variety or a related variety, and can reveal genetic differences between plants, as well as between plant parts, which can be genetically different as a result of an event comprising, for example, a backcross conversion, transgene, genetic sterility factor. Molecular marker profiling can also be used to reveal or validate, for example, a pedigree or genetic relationship among tested materials. Such molecular marker profiling can be accomplished by using a variety of techniques including, but not limited to, restriction fragment length polymorphism (RFLP), amplified fragment length polymorphism (AFLP), sequence-tagged sites (STS), randomly amplified polymorphic DNA (RAPD), arbitrarily primed polymerase chain reaction (AP-PCR), DNA amplification fingerprinting (DAF), sequence characterized amplified regions (SCARs), variable number tandem repeat (VNTR), short tandem repeat (STR), single feature polymorphism (SFP), simple sequence length polymorphism (SSLP), restriction site associated DNA, allozymes, isozyme markers, single nucleotide polymorphisms (SNPs), or simple sequence repeat (SSR) markers, also known as microsatellites (Gupta et al., 1999; Korzun et al., 2001). Various types of these marker platforms, for example, can be used to identify individual varieties developed from specific parent varieties, as well as cells, or other plant parts thereof. See, for example, Tyagi et al. (2014) "Genetic diversity and population structure in the US Upland cotton (*Gossypium hirsutum* L.)," *Theoretical and Applied Genetics* 127(2):283-295; Tatineni et al. (1996) "Genetic diversity in elite cotton germplasm determined by morphological characteristics and RAPDs," *Crop Science* 36(1):186-192; and Cho et al. (2014) "Genome-wide SNP marker panel applicable to Cotton Genetic diversity test,"

Proceedings of the International Cotton Genome Initiative Conference 2(1):11, each of which are incorporated by reference herein in their entirety.

In some examples, one or more markers may be used to examine and/or evaluate genetic characteristics of a cotton variety. Particular markers used for these purposes are not limited to any particular set of markers and diagnostic platforms, but are envisioned to include any type of markers and diagnostic platforms that can provide means for distinguishing varieties. One method of genetic characterization may to use only homozygous loci for cotton variety 16R246NRB2XF.

Primers and PCR protocols for assaying these and other markers are disclosed in, for example, CottonGen located on the World Wide Web at cottongen.org. In addition to being used for identification of cotton variety 16R246NRB2XF, as well as plant parts and plant cells of cotton variety 16R246NRB2XF, a genetic profile may be used to identify a cotton plant produced through the use of cotton variety 16R246NRB2XF or to verify a pedigree for progeny plants produced through the use of cotton variety 16R246NRB2XF. A genetic marker profile may also be useful in breeding and developing backcross conversions.

In an embodiment, the present invention provides a cotton plant characterized by molecular and physiological data obtained from a representative sample of said variety deposited with the American Type Culture Collection (ATCC). Thus, plants, seeds, or parts thereof, having all or essentially all of the morphological and physiological characteristics of cotton variety 16R246NRB2XF are provided. Further provided is a cotton plant formed by the combination of the disclosed cotton plant or plant cell with another cotton plant or cell and comprising the homozygous alleles of the variety.

In some examples, a plant, a plant part, or a seed of cotton variety 16R246NRB2XF may be characterized by producing a molecular profile. A molecular profile may include, but is not limited to, one or more genotypic and/or phenotypic profile(s). A genotypic profile may include, but is not limited to, a marker profile, such as a genetic map, a linkage map, a trait maker profile, a SNP profile, an SSR profile, a genome-wide marker profile, a haplotype, and the like. A molecular profile may also be a nucleic acid sequence profile, and/or a physical map. A phenotypic profile may include, but is not limited to, a protein expression profile, a metabolic profile, an mRNA expression profile, and the like.

One means of performing genetic marker profiling is using SSR polymorphisms that are well known in the art. A marker system based on SSRs can be highly informative in linkage analysis relative to other marker systems, in that multiple alleles for a given locus may be present. Another advantage of this type of marker is that through use of flanking primers, collecting more informative SSR data can be relatively easily achieved, for example, by using the polymerase chain reaction (PCR), thereby eliminating the need for labor-intensive Southern hybridization. PCR detection may be performed using two oligonucleotide primers flanking the polymorphic segment of repetitive DNA to amplify the SSR region.

Following amplification, genotype of test material revealed by each marker can be scored by electrophoresis of the amplification products. Scoring of marker genotype is based on the size of the amplified fragment, which correlates to the number of base pairs of the fragment. While variations in primers or laboratory procedures can affect the reported fragment size, the relative values should remain constant. When comparing multiple varieties, it may be beneficial to have all profiles performed in the same lab. Primers that can be used are publically available and may be found in, for example, CottonGen (Yu et al., CottonGen: a genomics, genetics and breeding database for cotton research," *Nucleic Acids Research* 42 (D1):D1229-D1236, 2013).

A genotypic profile of cotton variety 16R246NRB2XF can be used to identify a plant comprising variety 16R246NRB2XF as a parent, since such plants will comprise the same homozygous alleles as variety 16R246NRB2XF. Because the cotton variety at inbred stage is essentially homozygous at all relevant loci, most loci should have only one type of allele present. In contrast, a genetic marker profile of an $F_1$ progeny should be the sum of those parents. For example, if one parent was homozygous for allele X at a particular locus and the other parent homozygous for allele Y at that locus, the $F_1$ progeny will be XY (heterozygous) at that locus and the subsequent generations of progeny produced by selection and breeding are expected to be of genotype XX (homozygous), YY (homozygous), or XY (heterozygous) at that locus. When the $F_1$ plant is selfed or sibbed for successive filial generations, that locus should be either XX or YY.

In addition, plants and plant parts substantially benefiting from the use of variety 16R246NRB2XF in their development, such as variety 16R246NRB2XF comprising a backcross conversion, transgene, or genetic sterility factor, may be identified by having a molecular marker profile with a high percent identity to cotton variety 16R246NRB2XF. Such a percent identity might be 90%, 91%, 92%, 93%, 94%, 95%, 96%, 97%, 98%, 99%, 99.5% or 99.9% identical to cotton variety 16R246NRB2XF.

A genotypic profile of variety 16R246NRB2XF also can be used to identify essentially derived varieties and other progeny varieties developed from the use of variety 16R246NRB2XF, as well as cells and other plant parts thereof. Plants of the invention include any plant having at least 90%, 91%, 92%, 93%, 94%, 95%, 96%, 97%, 98%, 99%, 99.5%, or 99.9% of the markers in the genotypic profile, and that retain 90%, 91%, 92%, 93%, 94%, 95%, 96%, 97%, 98%, 99%, 99.5%, or 99.9% of the morphological and physiological characteristics of variety 16R246NRB2XF when grown under the same conditions. Such plants may be developed using markers well known in the art. Progeny plants and plant parts produced using variety 16R246NRB2XF may be identified, for example, by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from cotton variety 16R246NRB2XF, as measured by either percent identity or percent similarity. Such progeny may be further characterized as being within a pedigree distance of variety 16R246NRB2XF, such as within 1, 2, 3, 4, or 5 or less cross-pollinations to a cotton plant other than variety 16R246NRB2XF, or a plant that has variety 16R246NRB2XF as a progenitor. Unique molecular profiles may be identified with other molecular tools, such as SNPs and RFLPs.

The two cotton species commercially grown in the United States are *Gossypium hirsutum*, commonly known as short staple or upland cotton and *Gossypium barbadense*, commonly known as extra-long staple (ELS) or, in the United States, as Pima cotton. Upland cotton fiber is used in a wide array of coarser spin count products. Pima cotton is used in finer spin count yarns (50-80) which are primarily used in more expensive garments. Other properties of Pima cotton are critical because of fiber end use.

Cotton is an important and valuable field crop. Thus, a continuing goal of plant breeders is to develop stable, high yielding cotton varieties that are agronomically sound. The reasons for this goal are obviously to maximize the amount and quality of the fiber produced on the land used and to supply fiber, oil and food for animals and humans. To accomplish this goal, the cotton breeder must select and develop plants that have the traits that result in superior cultivars.

Improvement of Cotton Varieties

In certain further aspects, the invention provides plants modified to include at least a first trait. Such plants may, in one embodiment, be developed by a plant breeding technique called backcrossing, wherein essentially all of the morphological and physiological characteristics of a variety are recovered in addition to a genetic locus transferred into the hybrid via the backcrossing technique. The term backcrossing as used herein refers to the repeated crossing of a hybrid progeny back to a starting variety into which introduction of a trait is being carried out. The parental plant which contributes the locus or loci for a trait is termed the nonrecurrent or donor parent. This terminology refers to the fact that the nonrecurrent parent is used one time in the backcross protocol and therefore does not recur.

The parental cotton plant to which the locus or loci from the nonrecurrent parent are transferred is known as the recurrent parent as it is used for several rounds in the backcrossing protocol (Poehlman and Sleper, In: *Breeding Field Crops,* Iowa State University Press, Ames, 1995; Sprague and Dudley, In: *Corn and Improvement,* 3rd ed., 1988; Fehr, In: *Principles of variety development,* Theory and Technique (Vol 1) and Crop Species Soybean (Vol 2), Iowa State Univ., Macmillian Pub. Co., NY, 360-376, 1987b; Fehr, In: *Soybeans: Improvement, Production and Uses,* 2d Ed., *Monograph* 16:249, 1987). In a typical backcross protocol, the original line of interest (recurrent parent) is crossed to a second variety (nonrecurrent parent) that carries the genetic locus to be transferred. The resulting progeny from this cross are then crossed again to the recurrent parent and the process is repeated until a cotton plant is obtained wherein essentially all of the morphological and physiological characteristics of the recurrent parent are recovered in the converted plant, in addition to the transferred locus from the nonrecurrent parent.

The backcross process may be accelerated by the use of genetic markers, such as Simple Sequence Length Polymorphisms (SSLPs) (Williams et al., *Nucleic Acids Res.,* 18:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280:1077-1082, 1998) to identify plants with the greatest genetic complement from the recurrent parent.

The selection of a suitable recurrent parent is an important step for a successful backcrossing procedure. The goal of a backcross protocol is to add or substitute one or more new traits in a variety. To accomplish this, a genetic locus of the recurrent parent is modified or substituted with a locus from the nonrecurrent parent, while retaining essentially all of the rest of the genetic, and therefore the morphological and physiological constitution of the original variety. The choice of the particular nonrecurrent parent will depend on the purpose of the backcross; one possible purpose is to add some commercially relevant, agronomic trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the characteristic has been transferred.

Many traits have been identified that are not regularly selected for in the development of a new variety but that can be improved by backcrossing techniques. A genetic locus conferring the traits may or may not be transgenic. Examples of such traits known to those of skill in the art include, but are not limited to, male sterility, herbicide tolerance, resistance for bacterial, fungal, or viral disease, insect or nematode resistance, male sterility, ease of transformation, resistance to abiotic stresses and improved fiber characteristics. These genes are generally inherited through the nucleus, but may be inherited through the cytoplasm.

Direct selection may be applied where a genetic locus acts as a dominant trait. An example of a dominant trait is the herbicide tolerance trait. For this selection process, the progeny of the initial cross are sprayed with the herbicide prior to the backcrossing. The spraying eliminates any plants which do not have the herbicide tolerance characteristic, and only those plants which have the herbicide tolerance gene are used in the subsequent backcross. This process is then repeated for all additional backcross generations.

Many useful traits are those which are introduced by genetic transformation techniques. Methods for the genetic transformation of cotton are known to those of skill in the art, (see, e. g. Firoozabady et al., *Plant Mol. Biol.,* 10:105-116, 1987). For example, broadly applicable plant transformation methods which have been described include *Agrobacterium*-mediated transformation, microprojectile bombardment, electroporation, and direct DNA uptake by protoplasts.

*Agrobacterium*-mediated transfer is a widely applicable system for introducing gene loci into plant cells, including cotton. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium,* allowing for convenient manipulations (Klee et al., *Bio. Tech.,* 3(7): 637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio. Tech.,* 3(7):629-635, 1985; U.S. Pat. No. 5,563,055). One efficient means for transformation of cotton in particular is transformation and regeneration of cotton hypocotyl explants following inoculation with *Agro-*

*bacterium tumefaciens* from primary callus development, embryogenesis, embryogenic callus identification, transgenic cotton shoot production and the development of transgenic plants, as is known in the art.

To effect transformation by electroporation, for example, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner. Protoplasts may also be employed for electroporation transformation of plants (Bates, *Mol. Biotechnol.*, 2(2):135-145, 1994; Lazzeri, *Methods Mol. Biol.*, 49:95-106, 1995). For example, the generation of transgenic cotyledon-derived protoplasts was described by Dhir and Widholm in Intl. Patent Appl. Publ. No. WO 92/17598, the disclosure of which is specifically incorporated herein by reference. When protoplasts are used, transformation can also be achieved using methods based on calcium phosphate precipitation, polyethylene glycol treatment, and combinations of these treatments (see, e.g., Potrykus et al., *Mol. Gen. Genet.*, 199(2):169-177, 1985; Omirulleh et al., *Plant Mol. Biol.*, 21(3):415-428, 1993; Fromm et al., *Nature*, 319(6056):791-793, 1986; Uchimiya et al., *Mol. Gen. Genet.*, 204(2):204-207, 1986; Marcotte and Bayley, *Nature*, 335(6189):454-457, 1988).

Microprojectile bombardment is another efficient method for delivering transforming DNA segments to plant cells. In this method, particles are coated with nucleic acids and delivered into cells by a propelling force. Exemplary particles include those comprised of tungsten, platinum, and often, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

Microprojectile bombardment techniques are widely applicable, and may be used to transform virtually any plant species. The application of microprojectile bombardment for the transformation of cotton is described, for example, in Rajasekaran et al., *Mol. Breed.*, 2:307-319, 1996. An illustrative embodiment of a method for microprojectile bombardment is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Included among various plant transformation techniques are methods permitting the site-specific modification of a plant genome. These modifications can include, but are not limited to, site-specific mutations, deletions, insertions, and replacements of nucleotides. These modifications can be made anywhere within the genome of a plant, for example, in genomic elements, including, among others, coding sequences, regulatory elements, and non-coding DNA sequences. Any number of such modifications can be made and that number of modifications may be made in any order or combination, for example, simultaneously all together or one after another. Such methods may lead to changes in phenotype. The techniques for such modifications are well known in the art and include, for example, use of CRISPR-Cas systems, zinc-finger nucleases (ZFNs), and transcription activator-like effector nucleases (TALENs), among others.

It is understood to those of skill in the art that a locus of transgenic origin need not be directly transformed into a plant, as techniques for the production of stably transformed cotton plants that pass single loci to progeny by Mendelian inheritance is well known in the art. Such single loci may therefore be passed from parent plant to progeny plants by standard plant breeding techniques that are well known in the art. Non-limiting examples of traits that may be introduced directly or by backcrossing are presented below.

A. Male Sterility

Male sterility genes can increase the efficiency with which hybrids are made, in that they eliminate the need to physically emasculate the plant used as a female in a given cross. Where one desires to employ male-sterility systems, it may be beneficial to also utilize one or more male-fertility restorer genes. For example, where cytoplasmic male sterility (CMS) is used, hybrid crossing requires three inbred lines: (1) a cytoplasmically male-sterile line having a CMS cytoplasm; (2) a fertile inbred with normal cytoplasm, which is isogenic with the CMS line for nuclear genes ("maintainer line"); and (3) a distinct, fertile inbred with normal cytoplasm, carrying a fertility restoring gene ("restorer" line). The CMS line is propagated by pollination with the maintainer line, with all of the progeny being male sterile, as the CMS cytoplasm is derived from the female parent. These male sterile plants can then be efficiently employed as the female parent in hybrid crosses with the restorer line, without the need for physical emasculation of the male reproductive parts of the female parent.

The presence of a male-fertility restorer gene results in the production of fully fertile $F_1$ hybrid progeny. If no restorer gene is present in the male parent, male-sterile hybrids are obtained. Examples of male-sterility genes and corresponding restorers which could be employed with the plants of the invention are well known to those of skill in the art of plant breeding. Examples of such genes include CMS-D2-2, CMS-hir, CMS-D8, CMS-D4, and CMS-Cl. Fertility can be restored to CMS-D2-2 by the D2 restorer in which the restorer factor(s) was introduced from the genome of *G. harknessii* Brandegee (D2-2). Microsporogenesis in both CMS systems aborts during the premeiotic stage. One dominant restorer gene from the D8 restorer was identified to restore fertility of CMS-D8. The D2 restorer for CMS-D2-2 also restores the fertility of CMS-D8, CMS-hir, and CMS-Cl.

B. Herbicide Tolerance

Numerous herbicide tolerance genes are known and may be employed with the invention. A non-limiting example is a gene conferring resistance to a herbicide that inhibits the growing point or meristem such as imidazolinone or sulfonylurea herbicides. As imidazolinone and sulfonylurea herbicides are acetolactate synthase (ALS)-inhibiting herbicides that prevent the formation of branched chain amino acids, exemplary genes in this category code for ALS and AHAS enzymes as described, for example, by Lee et al., EMBO J., 7:1241, 1988; Gleen et al., Plant Molec. Biology, 18:1185, 1992; and Miki et al., Theor. Appl. Genet., 80:449, 1990. As a non-limiting example, a gene may be employed to confer resistance to the exemplary sulfonylurea herbicide nicosulfuron.

Resistance genes for glyphosate (resistance conferred by mutant 5-enolpyruvylshikimate-3-phosphate synthase (EPSPS) and aroA genes, respectively) and other phosphono compounds such as glufosinate (phosphinothricin acetyltransferase (PAT) and *Streptomyces hygroscopicus* phosphinothricin acetyltransferase (bar) genes) may also be used. See, for example, U.S. Pat. No. 4,940,835 to Shah et al., which discloses the nucleotide sequence of a form of EPSPS that can confer glyphosate resistance. Non-limiting examples of EPSPS transformation events conferring glyphosate resistance are provided by U.S. Pat. Nos. 6,040,497 and 7,632,985. The MON89788 event disclosed in U.S. Pat. No. 7,632,985 in particular is beneficial in conferring glyphosate tolerance in combination with an increase in average yield relative to prior events.

A DNA molecule encoding a mutant aroA gene can be obtained under ATCC Accession No. 39256, and the nucleotide sequence of the mutant gene is disclosed in U.S. Pat. No. 4,769,061 to Comai. A hygromycin B phosphotransferase gene from *E. coli* that confers resistance to glyphosate in tobacco callus and plants is described in Penaloza-Vazquez et al., Plant Cell Reports, 14:482, 1995. European Patent Application Publication No. EP0333033 to Kumada et al., and U.S. Pat. No. 4,975,374 to Goodman et al., disclose nucleotide sequences of glutamine synthetase genes that confer resistance to herbicides such as L-phosphinothricin. The nucleotide sequence of a phosphinothricin acetyltransferase gene is provided in European Patent Application Publication No. EP0242246 to Leemans et al. DeGreef et al. (Biotechnology, 7:61, 1989) describe the production of transgenic plants that express chimeric bar genes coding for phosphinothricin acetyl transferase activity. Exemplary genes conferring resistance to a phenoxy class herbicide haloxyfop and a cyclohexanedione class herbicide sethoxydim are the Acct-S1, Acct-S2 and Acct-S3 genes described by Marshall et al., (Theor. Appl. Genet., 83:435, 1992). As a non-limiting example, a gene may confer resistance to other exemplary phenoxy class herbicides that include, but are not limited to, quizalofop-p-ethyl and 2,4-dichlorophenoxyacetic acid (2,4-D).

Genes are also known that confer resistance to herbicides that inhibit photosynthesis such as, for example, triazine herbicides (psbA and gs+ genes) and benzonitrile herbicides (nitrilase gene). As a non-limiting example, a gene may confer resistance to the exemplary benzonitrile herbicide bromoxynil. Przibila et al. (Plant Cell, 3:169, 1991) describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al. (Biochem. J., 285:173, 1992). 4-hydroxyphenylpyruvate dioxygenase (HPPD) is a target of the HPPD-inhibiting herbicides, which deplete plant plastoquinone and vitamin E pools. Rippert et al. (Plant Physiol., 134:92, 2004) describes an HPPD-inhibitor resistant tobacco plant that was transformed with a yeast-derived prephenate dehydrogenase (PDH) gene. Protoporphyrinogen oxidase (PPO) is the target of the PPO-inhibitor class of herbicides; a PPO-inhibitor resistant PPO gene was recently identified in *Amaranthus tuberculatus* (Patzoldt et al., PNAS, 103(33):12329, 2006). The herbicide methyl viologen inhibits CO2 assimilation. Foyer et al. (Plant Physiol., 109:1047, 1995) describe a plant overexpressing glutathione reductase (GR) that is resistant to methyl viologen treatment.

Siminszky (Phytochemistry Reviews, 5:445, 2006) describes plant cytochrome P450-mediated detoxification of multiple, chemically unrelated classes of herbicides. Modified bacterial genes have been successfully demonstrated to confer resistance to atrazine, a herbicide that binds to the plastoquinone-binding membrane protein QB in photosystem II to inhibit electron transport. See, for example, studies by Cheung et al. (PNAS, 85:391, 1988), describing tobacco plants expressing the chloroplast psbA gene from an atrazine-resistant biotype of *Amaranthus hybridus* fused to the regulatory sequences of a nuclear gene, and Wang et al. (Plant Biotech. J., 3:475, 2005), describing transgenic alfalfa, *Arabidopsis*, and tobacco plants expressing the atzA gene from *Pseudomonas* sp. that were able to detoxify atrazine.

Bayley et al. (Theor. Appl. Genet., 83:645, 1992) describe the creation of 2,4-D-resistant transgenic tobacco and cotton plants using the 2,4-D monooxygenase gene tfdA from *Alcaligenes eutrophus* plasmid pJP5. U.S. Patent Application Publication No. 20030135879 describes the isolation of a gene for dicamba monooxygenase (DMO) from *Psueodmonas maltophilia* that is involved in the conversion of dicamba to a non-toxic 3,6-dichlorosalicylic acid and thus may be used for producing plants tolerant to this herbicide.

Other examples of herbicide resistance have been described, for instance, in U.S. Pat. Nos. 6,803,501; 6,448,476; 6,248,876; 6,225,114; 6,107,549; 5,866,775; 5,804,425; 5,633,435; 5,463,175.

C. Disease Resistance

Plant defenses are often activated by specific interaction between the product of a disease resistance gene (R) in the plant and the product of a corresponding avirulence (Avr) gene in the pathogen. A plant line can be transformed with cloned resistance gene to engineer plants that are resistant to specific pathogen strains. See, for example Jones et al., Science, 266:789, 1994 (cloning of the tomato Cf-9 gene for resistance to *Cladosporium flavum*); Martin et al., Science, 262:1432, 1993 (tomato Pto gene for resistance to *Pseudomonas syringae* pv.); Mindrinos et al., Cell, 78:1089, 1994 (*Arabidopsis* RPS2 gene for resistance to *Pseudomonas syringae*). Logemann et al., (Bio/technology, 10:305, 1992), for example, disclose transgenic plants expressing a barley ribosome-inactivating gene have an increased resistance to fungal disease.

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived, as well as by related viruses. See Beachy et al., Ann. Rev. Phytopathol., 28:451, 1990. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus.

A virus-specific antibody may also be used. See, for example, Tavladoraki et al., (Nature, 366:469, 1993), who show that transgenic plants expressing recombinant antibody genes are protected from virus attack. Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or increasing salicylic acid production (Ryals et al., Plant Cell, 8:1809-1819, 1996).

Plant defensins may be used to provide resistance to fungal pathogens (Thomma et al., Planta, 216:193-202, 2002).

Nematode resistance has been described, for example, in U.S. Pat. No. 6,228,992 and bacterial disease resistance in U.S. Pat. No. 5,516,671.

D. Insect Resistance

One example of an insect resistance gene includes a *Bacillus thuringiensis* protein, a derivative thereof, or a synthetic polypeptide modeled thereon. See, for example, Geiser et al., (*Gene*, 48:109, 1986), who disclose the cloning and nucleotide sequence of a Bt δ-endotoxin gene. Moreover, DNA molecules encoding δ-endotoxin genes can be purchased from the American Type Culture Collection, Manassas, Va., for example, under ATCC Accession Nos. 40098, 67136, 31995 and 31998. Another example is a lectin. See, for example, Van Damme et al., (*Plant Molec. Biol.*, 24:25, 1994), who disclose the nucleotide sequences of several *Clivia miniata* mannose-binding lectin genes. A vitamin-binding protein may also be used, such as avidin. See PCT application US93/06487, the contents of which are hereby incorporated by reference. This application teaches the use of avidin and avidin homologues as larvicides against insect pests.

Yet another insect resistance gene is an enzyme inhibitor, for example, a protease or proteinase inhibitor or an amylase inhibitor. See, for example, Abe et al., *J. Biol. Chem.*, 262:16793, 1987 (nucleotide sequence of rice cysteine proteinase inhibitor), Huub et al., *Plant Molec. Biol.*, 21:985, 1993 (nucleotide sequence of cDNA encoding tobacco proteinase inhibitor I), and Sumitani et al., *Biosci. Biotech. Biochem.*, 57:1243, 1993 (nucleotide sequence of *Streptomyces nitrosporeus* α-amylase inhibitor).

An insect-specific hormone or pheromone may also be used. See, for example, Hammock et al., (*Nature*, 344:458, 1990) disclosing baculovirus expression of cloned juvenile hormone esterase, an inactivator of juvenile hormone, Gade and Goldsworthy (*Eds. Physiological System in Insects*, Elsevier Academic Press, Burlington, Mass., 2007), describing allostatins and their potential use in pest control; and Palli et al. (*Vitam. Horm.*, 73:59-100, 2005), disclosing use of ecdysteroid and ecdysteroid receptor in agriculture. The diuretic hormone receptor (DHR) was identified in Price et al. (*Insect Mol. Biol.*, 13:469-480, 2004) as a candidate target of insecticides.

Still other examples include an insect-specific antibody or an immunotoxin derived therefrom and a developmental-arrestive protein. See Taylor et al., (Seventh Int'l Symposium on Molecular Plant-Microbe Interactions (Edinburgh, Scotland) Abstract #497, 1994), who described enzymatic inactivation in transgenic tobacco via production of single-chain antibody fragments.

E. Resistance to Abiotic Stresses

Abiotic stress includes dehydration or other osmotic stress, salinity, high or low light intensity, high or low temperatures, submergence, exposure to heavy metals, and oxidative stress. Delta-pyrroline-5-carboxylate synthetase (P5CS) from mothbean has been used to provide protection against general osmotic stress. Mannitol-1-phosphate dehydrogenase (mt1D) from *E. coli* has been used to provide protection against drought and salinity. Choline oxidase (codA from *Arthrobactor globiformis*) can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levansucrase (SacB) from yeast and *Bacillus subtilis*, respectively, can provide protection against drought (summarized from Annex II Genetic Engineering for Abiotic Stress Tolerance in Plants, Consultative Group On International Agricultural Research Technical Advisory Committee). Overexpression of superoxide dismutase can be used to protect against superoxides, as described in U.S. Pat. No. 5,538,878 to Thomas et al.

F. Modified Fatty Acid, Phytate, and Carbohydrate Metabolism

Genes may be used conferring modified fatty acid metabolism. For example, stearyl-ACP desaturase genes may be used. See Knutzon et al., *Proc. Natl. Acad. Sci. USA*, 89:2624, 1992. Various fatty acid desaturases have also been described, such as a *Saccharomyces cerevisiae* OLE1 gene encoding delta-9 fatty acid desaturase, an enzyme which forms the monounsaturated palmitoleic (16:1) and oleic (18:1) fatty acids from palmitoyl (16:0) or stearoyl (18:0) CoA (McDonough et al., *J. Biol. Chem.*, 267(9):5931-5936, 1992); a gene encoding a stearoyl-acyl carrier protein Δ9 desaturase from castor (Fox et al. *Proc. Natl. Acad. Sci. USA*, 90(6):2486-2490, 1993); Δ6 and Δ12 desaturases from the cyanobacteria *Synechocystis* responsible for the conversion of linoleic acid (18:2) to gamma-linolenic acid (18:3 gamma) (Reddy et al. *Plant Mol. Biol.*, 22(2):293-300, 1993); a gene from *Arabidopsis thaliana* that encodes an omega-3 desaturase (Arondel et al. *Science*, 258(5086):1353-1355, 1992); plant Δ9 desaturases (PCT Application Publ. No. WO 91/13972) and soybean and *Brassica* Δ15 desaturases (European Patent Application Publ. No. EP 0616644).

Phytate metabolism may also be modified by introduction of a phytase-encoding gene to enhance breakdown of phytate, adding more free phosphate to the transformed plant. For example, see Van Hartingsveldt et al., (*Gene*, 127:87, 1993), for a disclosure of the nucleotide sequence of an *Aspergillus niger* phytase gene. This, for example, could be accomplished by cloning and then reintroducing DNA associated with the single allele which is responsible for mutants characterized by low levels of phytic acid. See Raboy et al., (*Maydica*, 35:383, 1990).

A number of genes are known that may be used to alter carbohydrate metabolism. For example, plants may be transformed with a gene coding for an enzyme that alters the branching pattern of starch. See Shiroza et al., *J. Bacteol.*, 170:810, 1988 (nucleotide sequence of *Streptococcus mutans* fructosyltransferase gene), Steinmetz et al., *Mol. Gen. Genet.*, 20:220, 1985 (nucleotide sequence of *Bacillus subtilis* levansucrase gene), Pen et al., *BioTechnology*, 10:292, 1992 (production of transgenic plants that express *Bacillus licheniformis* α-amylase), Elliot et al., *Plant Molec. Biol.*, 21:515, 1993 (nucleotide sequences of tomato invertase genes), Sergaard et al., *J. Biol. Chem.*, 268:22480, 1993 (site-directed mutagenesis of barley α-amylase gene), and Fisher et al., *Plant Physiol.*, 102:1045, 1993 (maize endosperm starch branching enzyme II). The Z10 gene encoding a 10 kD zein storage protein from maize may also be used to alter the quantities of 10 kD zein in the cells relative to other components (Kirihara et al., *Mol. Gen. Genet.*, 211:477-484, 1988).

G. Improved Cotton Fiber Characteristics

Fiber characteristics such as fiber quality of quantity represent another example of a trait that may be modified in cotton varieties. For example, U.S. Pat. No. 6,472,588 describes transgenic cotton plants transformed with a sucrose phosphate synthase nucleic acid to alter fiber characteristics such as strength, length, fiber fineness, fiber maturity ratio, immature fiber content, fiber uniformity, and micronaire. Cotton plants comprising one or more genes coding for an enzyme selected from the group consisting of endoxyloglucan transferase, catalase and peroxidase for the improvement of cotton fiber characteristics are also described in U.S. Pat. No. 6,563,022. Cotton modification using ovary-tissue transcriptional factors preferentially directing gene expression in ovary tissue, particularly in very early fruit development, utilized to express genes encoding isopentenyl transferase in cotton ovule tissue and modify the characteristics of boll set in cotton plants and alter fiber quality characteristics including fiber dimension and strength is discussed in U.S. Pat. No. 6,329,570. A gene controlling the fiber formation mechanism in cotton plants is described in U.S. Pat. No. 6,169,174.

Genes involved in lignin biosynthesis are described by Dwivedi et al., *Mol. Biol.*, 26:61-71, 1994; Tsai et al., *Physiol.*, 107:1459, 1995; U.S. Pat. No. 5,451,514 (claiming the use of cinnamyl alcohol dehydrogenase gene in an antisense orientation such that the endogenous plant cinnamyl alcohol dehydrogenase gene is inhibited).

H. Additional Traits

Additional traits can be introduced into the cotton variety of the present invention. A non-limiting example of such a trait is a coding sequence which decreases RNA and/or protein levels. The decreased RNA and/or protein levels may be achieved through RNAi methods, such as those described in U.S. Pat. No. 6,506,559 to Fire and Mellow.

Another trait that may find use with the cotton variety of the invention is a sequence which allows for site-specific recombination. Examples of such sequences include the FRT sequence, used with the FLP recombinase (Zhu and Sadowski, *J. Biol. Chem.*, 270:23044-23054, 1995); and the LOX sequence, used with CRE recombinase (Sauer, *Mol. Cell. Biol.*, 7:2087-2096, 1987). The recombinase genes can be encoded at any location within the genome of the cotton plant, and are active in the hemizygous state.

It may also be desirable to make cotton plants more tolerant to or more easily transformed with *Agrobacterium tumefaciens*. Expression of p53 and iap, two baculovirus cell-death suppressor genes, inhibited tissue necrosis and DNA cleavage. Additional targets can include plant-encoded proteins that interact with the *Agrobacterium* Vir genes; enzymes involved in plant cell wall formation; and histones, histone acetyltransferases and histone deacetylases (reviewed in Gelvin, *Microbiology & Mol. Biol. Reviews*, 67:16-37, 2003).

Tissue Cultures and In Vitro Regeneration of Cotton Plants

A further aspect of the invention relates to tissue cultures of the cotton variety designated 16R246NRB2XF. As used herein, the term "tissue culture" indicates a composition comprising isolated cells of the same or a different type or a collection of such cells organized into parts of a plant. Exemplary types of tissue cultures are protoplasts, calli and plant cells that are intact in plants or parts of plants, such as embryos, pollen, flowers, leaves, roots, root tips, anthers, and the like. In one embodiment, the tissue culture comprises embryos, protoplasts, meristematic cells, pollen, leaves or anthers.

An important ability of a tissue culture is the capability to regenerate fertile plants. This allows, for example, transformation of the tissue culture cells followed by regeneration of transgenic plants. For transformation to be efficient and successful, DNA must be introduced into cells that give rise to plants or germ-line tissue.

Plants typically are regenerated via two distinct processes; shoot morphogenesis and somatic embryogenesis. Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses where some lines are more responsive to tissue culture manipulations than others. A line that is highly responsive in shoot morphogenesis may not generate many somatic embryos. Lines that produce large numbers of embryos during an induction step may not give rise to rapidly-growing proliferative cultures. Therefore, it may be desired to optimize tissue culture conditions for each cotton line. These optimizations may readily be carried out by one of skill in the art of tissue culture through small-scale culture studies. In addition to line-specific responses, proliferative cultures can be observed with both shoot morphogenesis and somatic embryogenesis. Proliferation is beneficial for both systems, as it allows a single, transformed cell to multiply to the point that it will contribute to germ-line tissue.

Embryogenic cultures can also be used successfully for regeneration, including regeneration of transgenic plants, if the origin of the embryos is recognized and the biological limitations of proliferative embryogenic cultures are understood. Biological limitations include the difficulty in developing proliferative embryogenic cultures and reduced fertility problems (culture-induced variation) associated with plants regenerated from long-term proliferative embryogenic cultures. Some of these problems are accentuated in prolonged cultures. The use of more recently cultured cells may decrease or eliminate such problems.

Definitions

In the description and tables herein, a number of terms are used. In order to provide a clear and consistent understanding of the specification and claims, the following definitions are provided:

A: When used in conjunction with the word "comprising" or other open language in the claims, the words "a" and "an" denote "one or more."

Agronomic Characteristics: Characteristics, which will vary from crop-to-crop and plant-to-plant, such as yield, maturity, pest resistance, and lint percent, and are relevant to the commercial success of a crop or plant. For example, agronomic characteristics for cotton include, but are not limited to, improved yield, maturity, fiber content, and fiber qualities.

Allele: Any of one or more alternative forms of a genetic locus. In a diploid cell or organism, the two alleles of a given gene occupy syntenic loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Disease Resistance: The ability of plants to restrict the activities of a specified pest, such as an insect, fungus, virus, or bacteria.

Disease Tolerance: The ability of plants to endure a specified pest (such as an insect, fungus, virus or bacteria) or an adverse environmental condition and still perform and produce in spite of this disorder.

Donor Parent: The parent of a variety which comprises a genetic locus, gene, or trait of interest which is to be introduced into a second variety.

Emasculate: The removal of plant male sex organs or the inactivation of the organs with a cytoplasmic or nuclear genetic factor conferring male sterility or a chemical agent.

Essentially all of the morphological and physiological characteristics: A plant having essentially all of the morphological and physiological characteristics of a designated plant has all of the characteristics of the plant that are otherwise present when compared in the same environment, other than an occasional variant trait that might arise during backcrossing or direct introduction of a transgene.

Extra Long Staple (ELS): The group classification for cotton in the longest staple length category. As used in practice and for commerce, ELS denotes varieties belonging to the species G. barbadense that have superior fiber qualities, including classification in the longest staple length category.

$F_1$ Hybrid: The first generation progeny of the cross of two nonisogenic plants.

Fallout (Fo): As used herein, the term "fallout" refers to the rating of how much cotton has fallen on the ground at harvest.

2.5% Fiber Span Length: Refers to the longest 2.5% of a bundle of fibers expressed in inches as measured by a digital fibergraph.

Fiber Characteristics: Refers to fiber qualities such as strength, fiber length, micronaire, fiber elongation, uniformity of fiber and amount of fiber.

Fiber Elongation: Sometimes referred to as "E1," refers to the elongation of the fiber at the point of breakage in the strength determination as measured by High Volume Instrumentation (HVI).

Fiber Span Length: The distance spanned by a specific percentage of fibers in a test specimen, where the initial starting point of the scanning in the test is considered 100 percent as measured by a digital fibergraph.

Fiber Strength: Also referred to as "T1," denotes the force required to break a bundle of fibers. Fiber strength is measured in millinewtons (mn) per tex on a stelometer.

Fruiting Nodes: The number of nodes on the main stem from which arise branches that bear fruit or boll in the first position.

Genotype: The genetic constitution of a cell or organism.

Gin Turnout: Refers to fraction of lint in a machine harvested sample of seed cotton (lint, seed, and trash).

Haploid: A cell or organism having one set of the two sets of chromosomes in a diploid.

Linkage: A phenomenon wherein alleles on the same chromosome tend to segregate together more often than expected by chance if their transmission was independent.

Lint Index: The weight of lint per seed in milligrams.

Lint Percent: Refers to the lint (fiber) fraction of seed cotton (lint and seed).

Lint Yield: Refers to the measure of the quantity of fiber produced on a given unit of land. Presented herein in pounds of lint per acre.

Lint/boll: As used herein, the term "lint/boll" is the weight of lint per boll.

Maturity Rating: A visual rating near harvest on the amount of open bolls on the plant. The rating range is from 1 to 5, 1 being early and 5 being late.

Micronaire: A measure of the fineness of the fiber. Within a cotton cultivar, micronaire is also a measure of maturity. Micronaire differences are governed by changes in perimeter or in cell wall thickness, or by changes in both. Within a variety, cotton perimeter is fairly consistent and maturity will cause a change in micronaire. Consequently, micronaire has a high correlation with maturity within a variety of cotton. Maturity is the degree of development of cell wall thickness. Micronaire may not have a good correlation with maturity between varieties of cotton having different fiber perimeter. Micronaire values range from about "2.0" to "6.0."

Phenotype: The detectable characteristics of a cell or organism, which characteristics are the manifestation of gene expression.

Plant Height: The average height in meters of a group of plants.

Quantitative Trait Loci (QTL): Genetic loci that control to some degree numerically representable traits that are usually continuously distributed.

Recurrent Parent: The repeating parent (variety) in a backcross breeding program. The recurrent parent is the variety into which a genetic locus, gene, or trait is to be introduced.

Regeneration: The development of a plant from tissue culture.

Seed/boll: Refers to the number of seeds per boll.

Seedcotton/boll: Refers to the weight of seedcotton per boll.

Seedweight: Refers to the weight of 100 seeds and is measured in grams.

Self-pollination: The transfer of pollen from the anther to the stigma of the same plant or a plant of the same genotype.

Single Locus Converted (Conversion) Plant: Plants which are developed by a plant breeding technique called backcrossing wherein essentially all of the morphological and physiological characteristics of a variety are recovered in addition to the characteristics conferred by the single locus transferred into the variety via the backcrossing technique. A single locus may comprise one gene, or in the case of transgenic plants, one or more transgenes integrated into the host genome at a single site (locus).

Stringout Rating: also sometimes referred to as "Storm Resistance" refers to a visual rating prior to harvest of the relative looseness of the seed cotton held in the boll structure on the plant. The rating values are from "1" to "5" (tight to loose in the boll).

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a cotton plant by genetic techniques, for example, genetic transformation.

Uniformity Ratio: A measure of the relative fiber span length uniformity of a bundle of fibers. The uniformity ratio is determined by dividing the 50% fiber span length by the 2.5% fiber span length.

Vegetative Nodes: The number of nodes from the cotyledonary node to the first fruiting branch on the main stem of the plant.

DEPOSIT INFORMATION

A deposit of the cotton variety 16R246NRB2XF, which is disclosed herein above and referenced in the claims, will be made with the American Type Culture Collection (ATCC), 10801 University Blvd., Manassas, Va. 20110-2209. The date of deposit is Jun. 14, 2019 and the accession number for those deposited seeds of cotton variety 16R246NRB2XF is ATCC Accession No. PTA-125987. All restrictions upon the deposit have been removed, and the deposit is intended to meet all of the requirements of the Budapest Treaty and 37 C.F.R. § 1.801-1.809. The deposit has been accepted under the Budapest Treaty and will be maintained in the depository for a period of 30 years, or 5 years after the last request, or for the effective life of the patent, whichever is longer, and will be replaced if necessary during that period.

The references cited herein, to the extent that they provide exemplary procedural or other details supplementary to those set forth herein, are specifically incorporated herein by reference.

What is claimed is:

1. A plant of cotton variety 16R246NRB2XF, wherein representative seed of said variety have been deposited under ATCC Accession No. PTA-125987.

2. A plant part of the plant of claim 1, wherein the plant part comprises at least one cell of the plant.

3. A seed that produces the plant of claim 1.

4. A method of producing cotton seed, wherein the method comprises crossing the plant of claim 1 with itself or a second, distinct cotton plant to produce the cotton seed.

5. The method of claim 4, wherein the method comprises crossing said plant with the second, distinct cotton plant to produce $F_1$ hybrid cotton seed.

6. An $F_1$ hybrid cotton seed produced by the method of claim 5.

7. A cotton plant produced by growing the $F_1$ hybrid cotton seed of claim 6.

8. The method of claim 5, wherein the method further comprises:
    (a) crossing a plant grown from the $F_1$ hybrid cotton seed with itself or a different cotton plant to produce seed of a subsequent generation;
    (b) growing a progeny plant of the subsequent generation from said seed and crossing the progeny plant with itself or a second plant to produce seed of a further subsequent generation; and
    (c) repeating step (b) with sufficient inbreeding to produce seed of an inbred cotton plant derived from cotton variety 16R246NRB2XF.

9. The method of claim 8, further comprising crossing a plant grown from said seed of an inbred cotton plant derived from cotton variety 16R246NRB2XF with a plant of a different genotype to produce seed of a hybrid cotton plant derived from cotton variety 16R246NRB2XF.

10. A composition comprising the seed of claim 3, wherein the seed is comprised in plant seed growth media.

11. The composition of claim 10, wherein the plant seed growth media is soil or a synthetic cultivation media.

12. A seed of cotton variety 16R246NRB2XF further comprising a single locus conversion, wherein representative seed of cotton variety 16R246NRB2XF have been deposited under ATCC Accession No. PTA-125987.

13. The seed of claim 12, wherein the single locus comprises a nucleic acid sequence that enables site-specific genetic recombination or confers a trait selected from the group consisting of male sterility, herbicide tolerance, insect or pest resistance, disease resistance, modified fatty acid metabolism, abiotic stress resistance, modified carbohydrate metabolism, and modified cotton fiber characteristics.

14. A plant grown from the seed of claim 12.

15. A seed of cotton variety 16R246NRB2XF further comprising a transgene, wherein representative seed of cotton variety 16R246NRB2XF have been deposited under ATCC Accession No. PTA-125987.

16. The seed of claim 15, wherein the transgene comprises a nucleic acid sequence that enables site-specific genetic recombination or confers a trait selected from the group consisting of male sterility, herbicide tolerance, insect or pest resistance, disease resistance, modified fatty acid metabolism, abiotic stress resistance, modified carbohydrate metabolism, and modified cotton fiber characteristics.

17. A plant grown from the seed of claim 15.

18. A method of modifying a cotton plant, wherein the method comprises introducing a transgene or a single locus conversion into the plant of claim 1.

19. A method of producing a commodity plant product, wherein the method comprises collecting the commodity plant product from the plant of claim 1.

20. A commodity plant product that is produced by the method of claim 19, wherein the commodity plant product comprises at least one cell of cotton variety 16R246NRB2XF.

\* \* \* \* \*